(12) United States Patent
Hoshino et al.

(10) Patent No.: US 6,696,293 B2
(45) Date of Patent: Feb. 24, 2004

(54) PROCESS FOR PRODUCING CAROTENOIDS AND BIOLOGICAL MATERIALS USEFUL THEREFOR

(75) Inventors: Tatsuo Hoshino, Kamakura (JP); Kazuyuki Ojima, Fujisawa (JP); Yutaka Setoguchi, Fujisawa (JP)

(73) Assignee: Roche Vitamins Inc., Parsippany, NJ (US)

( * ) Notice: Subject to any disclaimer, the term of this patent is extended or adjusted under 35 U.S.C. 154(b) by 299 days.

(21) Appl. No.: 09/864,894

(22) Filed: May 24, 2001

(65) Prior Publication Data

US 2003/0049720 A1 Mar. 13, 2003

(30) Foreign Application Priority Data

May 24, 2000 (EP) .............................................. 00111148

(51) Int. Cl.⁷ ........................... C12N 15/00; C12N 1/16; C07H 21/04
(52) U.S. Cl. .................. 435/440; 435/471; 435/254.11; 435/320.1; 536/23.1; 536/23.2; 536/23.7
(58) Field of Search ............................ 435/189, 254.11, 435/471, 67; 536/23.2, 23.1, 23.7

(56) References Cited

FOREIGN PATENT DOCUMENTS

| EP | 0 955 363 A2 | 11/1999 |
|----|--------------|---------|
| WO | WO 90/01552 | 2/1990 |
| WO | WO 91/02060 | 2/1991 |
| WO | WO 94/06918 | 3/1994 |
| WO | WO 97/23633 | 7/1997 |
| WO | WO 00/44920 | 8/2000 |

OTHER PUBLICATIONS

Database EMBL Sequence Database, Accession No.: XP–002176769, EMBL Sequence Database L46869 (1996).
Martinez, et al., "Genetic Transformation of Astaxanthin Mutants of *Phaffia rhodozyma*," *Antonie van Leeuwenhoek,* vol. 73, pp. 147–153 (1998).
Johnson and Schroeder, "Biotechnology of Astaxanthin Production in *Phaffia rhodozyma*," *Biotechnology for Improved Foods and Flavors,* vol. 637, pp. 39–50 (1996).
Li, et al., "Cloning and Analysis of the Alternative Oxidase Gene of *Neurospora crassa*," *Genetics,* vol. 142, No. 1, pp. 129–140 (1996).
An and Johnson, "Influence of light on growth and pigmentation of the yeast *Phaffia rhodozyma*," *Antonie van Leeuwenhoek,* vol. 57, pp. 191–203 (1990).
Schroeder and Johnson, "Singlet Oxygen and Peroxyl Radicals Regulate Carotenoid Biosynthesis in *Phaffia rhodozyma*," *The Journal of Biological Chemistry,* vol. 270, No. 1, pp. 18374–18379 (1995).
An, et al., Isolation of *Phaffia rhodozyma* Mutants with Increased Astaxanthin Content, *Applied and Environmental Microbiology,* vol. 55, No. 1, pp. 116–124 (1989).

*Primary Examiner*—Nashaat T. Nashed
(74) *Attorney, Agent, or Firm*—Bryan Cave LLP

(57) ABSTRACT

A process for producing carotenoids, which involves cultivating a microorganism obtained by treating a parent microorganism that produces carotenoids under conditions that induce a reduction in alternative oxidase activity and selecting a microorganism with enhanced carotenoid productivity, a method for obtaining the microorganism with enhanced carotenoid productivity, and the microorganism itself.

21 Claims, 1 Drawing Sheet

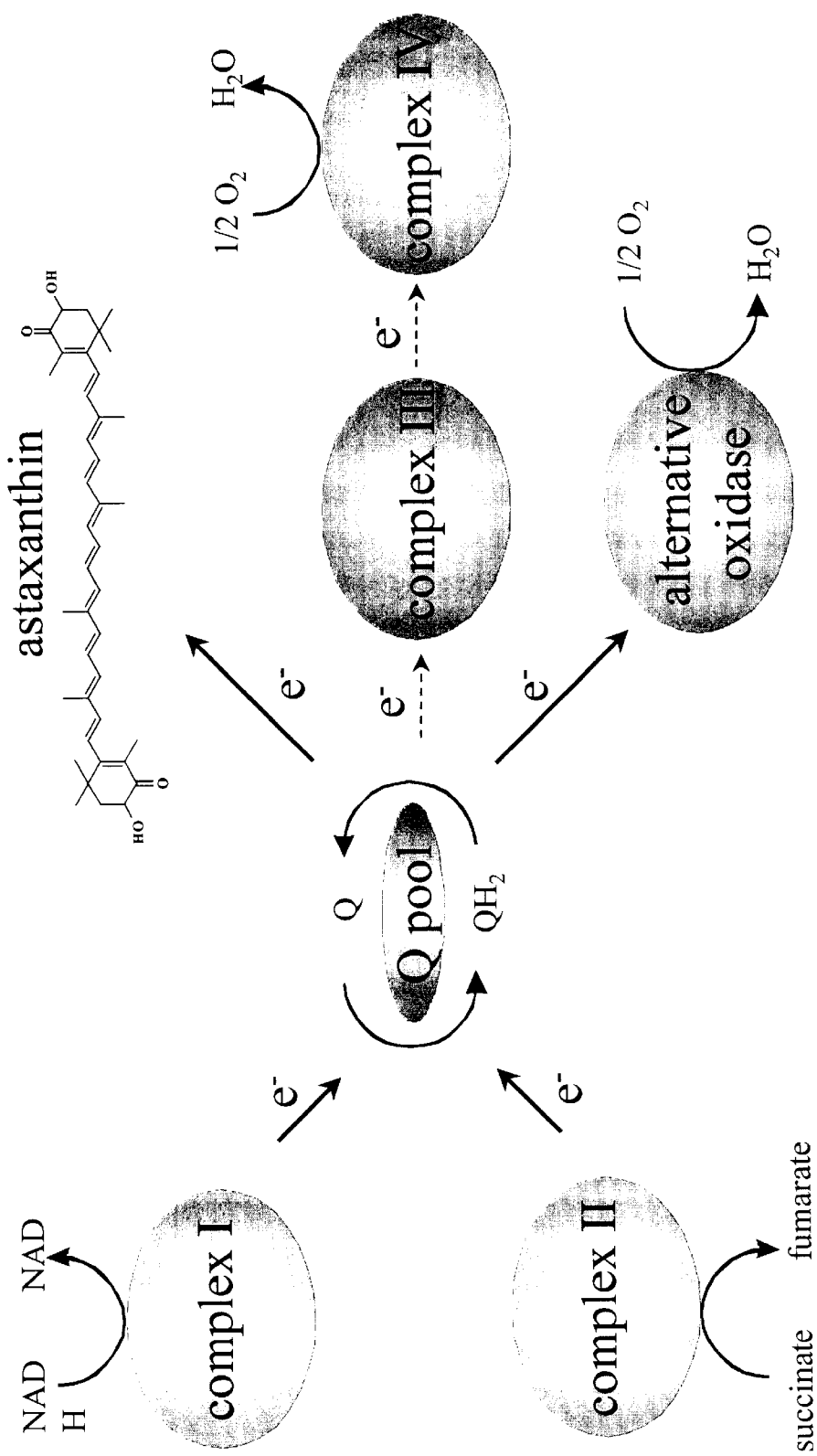
FIG. 1 Model for electron flow in the respiratory chain of *P. rhodozyma*

PROCESS FOR PRODUCING CAROTENOIDS AND BIOLOGICAL MATERIALS USEFUL THEREFOR

FIELD OF THE INVENTION

The present invention relates to the manufacture of carotenoids and biological materials useful therefor.

BACKGROUND OF THE INVENTION

Astaxanthin is known to be distributed in a wide variety of organisms, such as, for example, animals (e.g., birds, such as, for example, flamingos and scarlet ibis, and fish, such as, for example, rainbow trout and salmon), algae, and microorganisms. It is also recognized that astaxanthin possesses a strong antioxidation property against reactive oxygen species, which suggests a pharmaceutical applicability in protecting living cells against some diseases, such as, for example, cancer. Moreover, from a viewpoint of industrial application, demand for astaxanthin as a coloring reagent is increasing, especially in the industry of farmed fish, such as, for example, salmon, because astaxanthin imparts a distinctive orange-red coloration to the animals that contributes to consumer appeal in the marketplace.

*Phaffia rhodozyma* is known as a carotenogenic yeast strain that produces astaxanthin. In contrast to other carotenogenic yeast, such as, for example, Rhodotorula, *Phaffia rhodozyma* (*P. rhodozyma*) can ferment some sugars such as, for example, D-glucose. This is an important feature from the viewpoint of industrial application. In a recent taxonomic study, the sexual cycle of *P. rhodozyma* was revealed and its telemorphic state was designated under the name of *Xanthophyllomyces dendrorhous* (W. I. Golubev; Yeast 11, 101–110, 1995).

In order to obtain hyper-producers of astaxanthin from *P. rhodozyma*, some strain improvement studies have been conducted. However, in this decade, such efforts have been restricted to employing conventional mutagenesis and protoplast fusion techniques. Recently, Wery et al. developed a host vector system using *P. rhodozyma* in which multicopies of a non-replicable plasmid were integrated into the genome of *P. rhodozyma* at the ribosomal DNA locus (Wery et al., Gene, 184, 89–97, 1997). Verdoes et al., International Patent Publication No. WO97/23633, reported the use of improved vectors to transform *P. rhodozyma* with copies of the three carotenogenic genes that encode enzymes that catalyze the reaction from geranylgeranyl pyrophosphate to beta-carotene.

Many researchers have speculated that astaxanthin might function as an antioxidant in *Phaffia rhodozyma* because its production is stimulated during the respiration phase of growth rather than during the fermentation phase. In general, reactive oxygen species tend to be generated during the respiration phase as a result of electron overflow in the respiratory chain. Electron overflow in the respiratory chain is caused by an imbalance of electron transfer during reduction of the ubiquinone pool and electron transfer occurring downstream in the respiratory chain. It is speculated that astaxanthin might quench such reactive oxygen species in a manner analogous to superoxide dismutase.

Schroeder and Johnson reported that the respiratory chain of *Phaffia rhodozyma* shifted from KCN-sensitive respiration to KCN-resistant respiration during the late phase of growth when astaxanthin production was stimulated (J. Biol. Chem., 270, 18374–18379, 1995). The KCN-sensitive respiratory chain, in which an electron from the ubiquinone pool is transferred to complex IV via complex III, is a common electron transfer chain that is found in a wide variety of organisms. It is known that this respiratory chain is inhibited by KCN or antimycin A.

The KCN-resistant respiratory chain is found in both plants and fungi. In this respiratory chain, a mitochondrial membrane protein, alternative oxidase (AOX), plays a substantial role in transferring an electron from the ubiquinone pool to an $H_2O$ molecule by using an oxygen molecule as an acceptor. AOX activity is known to be inhibited by n-propyl gallate (n-PG) or salicylhydroxamic acid (SHAM).

In their characterization study of antimycin-sensitive hyper-producers of astaxanthin derived from *Phaffia rhodozyma*, An et al. speculated that such mutants produced increased amounts of astaxanthin to quench reactive oxygen species, which might be produced by electron overflow from the electron transfer chain (Appl. Env. Microbiol, 55, 116–124, 1989).

SUMMARY OF THE INVENTION

This invention was conceived based on the presumption that the biosynthesis of astaxanthin might be upregulated under conditions in which the electron transfer chain is in the reduced state. The reduced state might be induced by addition of a specific inhibitor such as antimycin A, KCN, n-PG or SHAM. The reduced state might also be induced by a mutation that would result in an imbalance in electron transfer.

In accordance with this invention, mutants were obtained that displayed resistance to SHAM. Surprisingly, these mutants displayed 50% higher productivity of astaxanthin than their parent strain.

In the present invention, the cloning of a gene that codes for an alternative oxidase from *Phaffia rhodozyma* is disclosed. In the present invention, the enzymatic characterization of the expression of the gene in suitable host organisms such as *E. coli* or *Saccharomyces cerevisiae* is also disclosed. The cloned gene may be used for the reduction of AOX activity using methods such as, for example, site-directed mutagenesis of promoter sequences or anti-sense methods in a suitable host, such as *P. rhodozyma*. The effects of gene expression on carotenogenesis can be studied by cultivating transformants in an appropriate medium under appropriate cultivation conditions.

An object of the present invention is a process for producing a carotenoid involving:

(a) culturing a mutant microorganism in culture medium containing an alternative oxidase (AOX) inhibitor, wherein the mutant microorganism produces at least 10% more of the carotenoid compared to the parental stain of the mutant microorganism; and (b) recovering the carotenoid produced by the mutant microorganism from the culture media.

Another object of the present invention is a process for producing a carotenoid involving:

(a) culturing a microorganism containing a polynucleotide sequence encoding an alternative oxidase (AOX), which polynucleotide sequence has been altered to form a mutant microorganism compared to a parental microorganism containing an unaltered polynucleotide sequence encoding AOX, which mutant microorganism has a reduced level of AOX expression and produces at least 10% more carotenoid as compared to the unaltered parental microorganism; and (b) recovering the carotenoid produced by the mutant microorganism.

A further object of the present invention is a process for engineering a carotenoid-producing microorganism involving:

(a) selecting a parental microorganism that produces a carotenoid;

(b) culturing the parental microorganism in a culture medium containing an alternative oxidase (AOX) inhibitor; and (c) selecting a mutant microorganism that grows in the culture medium containing the AOX inhibitor and which microorganism produces at least 10% more of the carotenoid compared to the parental microorganism.

A further object of the present invention is a process for engineering an enhanced carotenoid-producing microorganism involving:

(a) selecting a parental microorganism that produces a carotenoid;

(b) altering a polynucleotide sequence encoding an alternative oxidase (AOX) in the parental microorganism to form a mutant microorganism, which mutant has a reduced level of AOX expression compared to the parental microorganism; and (c) selecting a mutant microorganism that produces at least 10% more of the carotenoid compared to the parental microorganism.

Another object of the present invention is a recombinantly-produced mutant microorganism produced from a parental carotenoid-producing microorganism having a gene that encodes alternative oxidase (AOX), wherein the gene expression of the AOX in the parental microorganism is altered to produce the mutant microorganism, whereby the efficiency of expression of the AOX in the mutant is reduced compared to the parental microorganism and the mutant produces at least 10% more of a carotenoid compared to the parental microorganism.

A further object of the present invention is an isolated polynucleotide sequence encoding an alternative oxidase derived from a carotenoid-producing microorganism.

Another object of the present invention is a polypeptide having SEQ ID NO: 1 or a fragment of SEQ ID NO: 1 having AOX activity.

A further object of the present invention is a process for producing astaxanthin involving:

(a) cultivating in a culture medium a microorganism transformed with a vector containing an antisense polynucleotide sequence for a native alternate oxidase (AOX) gene in the microorganism, which microorganism produces astaxanthin at a level that is at least 10% greater than a parental strain of the microorganism that is not transformed with the vector; and (b) collecting the astaxanthin from the microorganism and/or the culture media.

Another object of the present invention is an astaxanthin-producing microorganism having a vector containing an antisense polynucleotide sequence for a native alternate oxidase (AOX) gene in the microorganism, which microorganism produces astaxanthin at a level that is at least 10% greater than a parental strain of the microorganism that is not transformed with the vector.

A further object of the present invention is a process for producing carotenoids, which involves cultivating a microorganism obtained by treating a parent microorganism that produces carotenoids under conditions that induce a reduction in the activity of an alternative oxidase, and selecting a microorganism with enhanced carotenoid productivity. The microorganism utilized in the process of the present invention may be a mutant strain in which carotenoid productivity is enhanced due to an altered resistance against the alternative oxidase inhibitor. The process according to the present invention can be practiced by using a microorganism belonging to the kingdom of Protista or Fungi, preferably to the genus Synechococcus, Synechocystis, Haematococcus, Dunaliella, Phaffia, Xanthophyllomyces, Neurospora, Rhodotorula, Blakeslea, or Phycomyces, more preferably the microorganism may be *Phaffia rhodozyma* or *Xanthophyllomyces dendrorhous*. The alternative oxidase inhibitor used in the present invention may be selected from n-propyl gallate and salicylhydroxamic acid.

Another object of the present invention is a method for establishing a mutant strain capable of producing carotenoids at an enhanced level relative to the parent microorganism. The method involves cultivating a microorganism that produces carotenoids under conditions that reduce the activity of an alternative oxidase and selecting for a microorganism capable of producing carotenoids at a higher level than the parent microorganism. The conditions that reduce alternative oxidase activity may involve the presence of an alternative oxidase inhibitor. The alternative oxidase inhibitor may be selected from n-propyl gallate and salicylhydroxamic acid. The microorganism may belong to the kingdom of Protista or Fungi, preferably to the genus Synechococcus, Synechocystis, Haematococcus, Dunaliella, Phaffia, Xanthophyllomyces, Neurospora, Rhodotorula, Blakeslea, or Phycomyces, more preferably the microorganism may be *Phaffia rhodozyma* or *Xanthophyllomyces dendrorhous*.

A further object of the present invention is a mutant strain capable of producing carotenoids at an enhanced level, relative to a parent microorganism, obtained by the method described above. The mutant may be more specifically characterized in that it can grow in a medium containing 0.3 to 0.45 mg/ml of SHAM at a growth rate comparable to the growth rate in a medium that does not contain SHAM.

An embodiment of the present invention is a SHAM-resistant mutant derived from *Phaffia rhodozyma* ATCC 96594. SHAM-resistant mutant strains have been deposited at the DSMZ (Deutsche Sammlung der Mikroorganismen und Zellkulturen GmbH, Mascheroder Weg 1b, D-38124 Braunschweig, Germany) under the designations DSM 13429, DSM 13430 and DSM 13431, on Apr. 3, 2000.

The microorganism used in the process of the present invention may be a recombinant microorganism in which gene expression of the alternative oxidase has been altered to reduce overall efficiency compared to the parent microorganism. Accordingly, another object of the invention is a recombinant microorganism capable of producing carotenoids at an enhanced level relative to the host microorganism, whose gene expression of the alternative oxidase has been altered to reduce overall efficiency compared to the host microorganism. The alternative oxidase gene expression of the host microorganism may be altered by using a genetic technique, such as, for example, antisense technology, site-directed mutagenesis, chemical mutagenesis, and other commonly used mutagenic techniques. The microorganism used for this purpose may belong to the kingdom of Protista or Fungi, preferably to the genus Synechococcus, Synechocystis, Haematococcus, Dunaliella, Phaffia, Xanthophyllomyces, Neurospora, Rhodotorula, Blakeslea, or Phycomyces, more preferably the microorganism may be *Phaffia rhodozyma* or *Xanthophyllomyces dendrorhous*, most preferably the microorganism may be one of the deposited strains, DSM 13429, DSM 13430 and DSM 13431.

A further object of the invention is a recombinant DNA sequence that encodes an alternative oxidase derived from a microorganism capable of producing carotenoids. The recombinant DNA may preferably be obtained from a microorganism which belongs to the kingdom of Protista or Fungi, more preferably the genus Synechococcus, Synechocystis, Haematococcus, Dunaliella, Phaffia, Xanthophyllomyces, Neurospora, Rhodotorula, Blakeslea, or Phycomyces, even more preferably the microorganism may be *Phaffia rhodozyma* or *Xanthophyllomyces dendrorhous*, most preferably the microorganism may be one of the deposited strains, DSM 13429, DSM 13430 and DSM 13431. The recombinant DNA sequence may be that identified by SEQ ID NO: 2 or may be a sequence having identity with SEQ ID NO: 2 higher than 55%, more preferably higher than 75%, such as, for example, higher than 95%.

The recombinant DNA sequence may be more specifically characterized in that it encodes (a) the enzyme having the amino acid sequence shown in SEQ ID NO: 1, or (b) a variant of the enzyme having the amino acid sequence shown in SEQ ID NO: 1 selected from (i) an allelic variant, and (ii) an enzyme having one or more (such as 1–50, 2–40, 3–30, 4–20 or 5–10) amino acid additions, insertions, deletions and/or substitutions and still having the stated enzymatic activity. The isolated DNA sequence may be derived from a gene of *Phaffia rhodozyma* and selected from (i) the DNA sequence shown in SEQ ID NO: 2, (ii) an isocoding or allelic variant of the DNA sequence shown in SEQ ID NO: 2, and (iii) a derivative of a DNA sequence shown in SEQ ID NO: 2, with additions, insertions, deletions and/or substitutions of one or more nucleotide(s), and coding for a polypeptide having the stated enzymatic activity.

Another object of the invention is the use of the recombinant DNA to transform a host microorganism. A convenient form of the recombinant DNA may be a vector. The recombinant microorganism obtained by use of the recombinant DNA should be capable of decreasing the enzyme activity of the alternative oxidase. The host microorganism transformed with the recombinant DNA may be useful in improving carotenoid production, in particular astaxanthin. Accordingly, another object of the invention is such a recombinant microorganism.

A further object of the invention is a method for the biological production of carotenoids, which involves introducing the recombinant DNA, as set forth above, into an appropriate host microorganism and cultivating the resulting recombinant microorganism under conditions conducive to the production of carotenoids. This method may preferably be applied to the biological production of astaxanthin.

SUMMARY OF THE DRAWING

FIG. 1 is a flow diagram of a working model for the respiratory chain of *P. rhodozyma*.

DETAILED DESCRIPTION OF THE INVENTION

Many researchers have speculated that astaxanthin is an antioxidant in *Phaffia rhodozyma* because its production is stimulated in the respiration phase of growth rather than in the fermentation phase. In general, reactive oxygen species tend to be produced in the respiration phase as a result of electron overflow in the respiratory chain that is caused by an imbalance of electron transfer during reduction of the ubiquinone pool and electron transfer occurring downstream in the respiratory chain (FIG. 1). It is speculated that astaxanthin might quench such reactive oxygen species in a manner analogous to superoxide dismutase.

Accordingly, the overproduction of astaxanthin may be realized by the inhibition of the respiratory chain in *Phaffia rhodozyma*. In fact, An et al. have isolated mutants of *Phaffia rhodozyma* whose KCN-sensitive respiration was blocked and which produced increased amounts of astaxanthin (Appl. Env. Microbiol, 55, 116–124, 1989).

On the other hand, Schroeder and Johnson reported that the respiratory chain of *Phaffia rhodozyma* was shifted from KCN-sensitive respiration to KCN-resistant respiration during the late phase of growth when astaxanthin production was stimulated (J. Biol. Chem., 270, 18374–18379, 1995). In this context, KCN-resistant respiration, which is mediated by an alternative oxidase, would have a greater effect on respiration during the production phase of astaxanthin. Thus, the inhibition of alternative oxidase might lead to the overproduction of astaxanthin.

In order to examine the effect of the specific inhibition of respiration activity on the production of astaxanthin in *Phaffia rhodozyma*, SHAM, which is known to inhibit the alternative oxidase, was added to growing *Phaffia rhodozyma* cells in an agar medium at serially diluted concentrations. In the course of this study, several spontaneous mutants appeared that showed growth activity in medium containing 0.3 to 0.45 mg/ml SHAM that was similar to growth activity in medium that did not contain SHAM. Surprisingly, it was found that such mutants produced 50% greater amounts of astaxanthin than their parent. This indicated that a mutation which led to the overproduction of astaxanthin complemented growth inhibition due to the reduced state of the respiratory chain caused by a decrease in alternative oxidase activity.

In the present invention, the terms "DNA" and "polynucleotide" are used interchangeably. Likewise, the terms "protein" and "polypeptide" are also used interchangeably.

The present invention provides isolated mutants that are resistant to 0.3 to 0.45 mg/ml of the specific inhibitor of alternative oxidase, SHAM. As set forth above, mutant strains with increased astaxanthin production may be obtained by cultivating appropriate microorganisms in the presence of any of the inhibitors of alternative oxidase, and screening the microorganisms growing in the presence of the inhibitor(s) for increased astaxanthin production relative to the parent microorganisms. Astaxanthin production may be assayed by extracting carotenoids from the cells of *P. rhodozyma* and measuring astaxanthin levels as exemplified in Example 2. An increase in productivity of about 10% is used to select a mutant strain capable of producing astaxanthin at a higher level relative to the parent strain. Re-cultivation and further screening of the obtained mutant strains under the pressure of the alternative oxidase inhibitor is used to further improve productivity. The obtained mutant strains was used to produce astaxanthin in an appropriate medium.

In order to decrease the activity of an alternative oxidase, an approach that employs genetic engineering techniques has several advantages compared to an approach based on the addition of a specific inhibitor, such as SHAM, to the culture medium. One of these advantages is economic. Addition of an inhibitor would increase production costs. A further disadvantage of adding an inhibitor to the culture medium is that it requires a further purification step in order to remove the added inhibitors from the final product.

The present invention also provides an isolated recombinant DNA sequence which encodes an alternative oxidase from *Phaffia rhodozyma*.

The DNA of the present invention includes a cDNA that contains only an open reading frame flanked between short fragments in its 5'- and 3'- untranslated region, and also includes a genomic DNA which contains its introns and regulatory sequences, such as, for example, its promoter and terminator, which are involved in the expression of the gene of interest.

Initially, we cloned a partial gene fragment containing a portion of the AOX gene using the degenerate PCR (Polymerase Chain Reaction) method. Degenerate PCR is a method used to clone a gene of interest that has high amino acid sequence homology to known enzymes from other species which have the same or similar functions. The primer used in degenerate PCR (i.e. the degenerate primer), was designed by reverse translation of an amino acid sequence to yield corresponding nucleotides ("degenerated"). A mixed primer which consists of A, C, G, or T, or a primer containing inosine at an ambiguity code, is generally used as the degenerate primer. In this invention, mixed primers were used to clone the gene, as set forth above. The PCR conditions used were varied depending on the primers used and the gene to be cloned, as described hereinafter.

An entire gene, including its coding region and its introns, as well as its regulatory regions, such as, for example, a promoter or terminator, can be cloned from a chromosome by screening a genomic library, constructed in phage vectors or plasmid vectors, and contained in an appropriate host. The library is screened with a partial DNA fragment obtained by degenerate PCR, as set forth above, as a probe after it has been labeled. Generally, E. coli is used as a host strain and an E. coli vector, such as, for example, a phage vector (e.g. lambda phage vector), or a plasmid vector (e.g. pUC vector) is used in the construction of the library following genetic manipulation, such as for example, sequencing, restriction digestion, ligation and other genetic manipulation techniques well known to one of skill in the art.

In this invention, an EcoRI genomic library of P. rhodozyma was constructed in a lambda vector derivative, lambda gt11. The lengths of the claimed inserts were determined by Southern blot hybridization prior to construction of the library. The DNA that was used as a probe was labeled with digoxigenin (DIG), a steroid hapten, instead of the conventional $^{32}P$ label, following the protocol which was provided by the supplier (Boehringer-Mannheim, Mannheim, Germany). A genomic library constructed from the chromosome of P. rhodozyma was screened using the DIG-labeled DNA fragment that contained a portion of the gene of interest, as a probe. Hybridized plaques were picked and used for further study. After the isolation of a positive plaque, the insert fragment was subcloned into an appropriate plasmid vector that could be conveniently used for sequencing. The insert fragment in the positive phage vector was subcloned into a pOCUS-2 vector, which was used for construction of transposon-inserted sequencing derivatives (Locus Pocus System, Novagene, Madison, U.S.A.).

The present invention used an automated fluorescent DNA sequencer, ALFred system (Pharmacia, Uppsala, Sweden), with an autocycle sequencing protocol using Taq DNA polymerase.

After the determination of the genomic sequence, the sequence of the coding region was used for cloning the cDNA of a corresponding gene. The PCR method was also used to clone the cDNA fragment. PCR primers whose sequences were identical to the sequences at the 5'- and 3'- ends of the open reading frame (ORF) were synthesized with the addition of an appropriate restriction site, and PCR was performed using these PCR primers. A cDNA pool was used as a template in the PCR cloning of the cDNA. The cDNA pool consisted of various cDNA species which were synthesized in vitro by viral reverse transcriptase and Taq polymerase (CapFinder Kit manufactured by Clontech, Palo Alto, U.S.A.), using the mRNA obtained from P. rhodozyma as a template. The cDNA of interest thus obtained can be confirmed via sequencing. Furthermore, the enzymatic activity of the polypeptide encoded by the cDNA of interest can be confirmed by cloning the cDNA fragment into an expression vector that functions in E. coli or S. cerevisiae, under the control of an appropriate promoter.

To express a gene derived from an eukaryote, a procedure in which the cDNA is cloned into an expression vector in E. coli or S. cerevisiae is often used. This is due to the specificity of intron structures that varies among microorganisms, and an inability of one species to recognize the intron sequence from another species. In fact, prokaryotes do not have introns. Even in yeast, the genetic background of Ascomycetes, of which Saccharomyces cerevisiae is a member, and Basidiomycetes, of which P. rhodozyma is a member, varies. Wery et al. showed that the intron structure of the actin gene from P. rhodozyma cannot be recognized, nor spliced, by the ascomycetous yeast, Saccharomyces cerevisiae (Yeast, 12, 641–651, 1996).

Other researchers have reported that the intron structures of some genes play a role in regulating their own gene expression (Dabeva, M. D. et al., Proc. Natl. Acad. Sci. U.S.A., 83, 5854, 1986). Thus, it might be important to use a genomic fragment which has its introns, in case the intron structure is involved in the regulation of its own gene expression.

In order to apply genetic engineering methods in a strain improvement study, it is necessary to study genetic mechanisms such as, for example, transcription and translation. In order to study these genetic mechanisms, it is not only important to determine the genetic sequence of the exon, but also the genetic sequence of upstream activation sequences (UAS), promoters, introns, and terminators.

The gene that codes for the alternative oxidase was cloned from the genomic DNA of P. rhodozyma, and the genomic sequence of the alternative oxidase (AOX) gene, including its 5'- and 3'-adjacent regions, as well as its intron structures, was determined. After the enzymatic activity is confirmed, gene modification studies can be conducted to decrease the alternative oxidase activity.

In the present invention, the polynucleotide sequence includes SEQ ID NO: 2 and fragments thereof encoding a polypeptide having AOX activity and polynucleotide sequences which hybridize to SEQ ID NO: 2 under stringency conditions which are sufficient to identify specific binding to SEQ ID NO: 2, and which hybrids encode a polypeptide that has the function of an alternative oxidase. For example, any combination of the following hybridization and wash conditions may be used to achieve the required specific binding:

High Stringency Hybridization:
  6× SSC
  0.5% SDS
  100 micrograms/ml denatured salmon sperm DNA
  50% formamide
  Incubate overnight with gentle rocking at 42° C. overnight.

High Stringency Wash:
  1 wash in 2× SSC, 0.5% SDS at Room Temperature for 15 minutes, followed by another wash in 0.1× SSC, 0.5% SDS at Room Temperature for 15 minutes.

Low Stringency Hybridization:
  6× SSC
  0.5% SDS
  100 micrograms/ml denatured salmon sperm DNA
  50% formamide
  Incubate overnight with gentle rocking at 37° C. overnight.
Low Stringency Wash:
  1 wash in 0.1× SSC, 0.5% SDS at Room Temperature for 15 minutes.

Moderately stringent conditions may be obtained by varying the temperature at which the hybridization reaction occurs and/or the wash conditions as set forth above. In the present invention, it is preferred to use high stringency hybridization and wash conditions.

Various genetic methods can be employed to decrease gene expression. One of such methods is the anti-sense method. The anti-sense method can be used to decrease the expression of a gene of interest by introducing an artificial gene fragment whose sequence is complementary to that of a gene of interest. The anti-sense gene fragment would form a complex with a mature mRNA fragment of the objective gene in vivo and as a consequence, inhibit the efficient translation of the complexed mRNA. In order to construct an anti-sense RNA for the AOX gene, the PCR method can be used to clone a complementary cDNA strand for the AOX gene.

Another genetic method is to create a mutation in the promoter region of the gene of interest. In general, a gene consists of several parts which have different functions from each other. In eukaryotes, some genes that encode proteins are transcribed to premature messenger RNA (pre-mRNA), which differs from the genes for ribosomal RNA (rRNA), small nuclear RNA (snRNA) and transfer RNA (tRNA). Although RNA polymerase II (PolII) plays a central role in this transcription event, PolI by itself cannot initiate transcription without cis elements, which cover an upstream region and contain a promoter and an UAS (Upstream Activating Sequence), and a trans-acting protein factor. Initially, a transcription initiation complex, which consists of several basic protein components, recognizes the promoter sequence located in the 5'-adjacent region of the gene to be expressed. During transcription initiation, some additional participants are required if the expressed gene is under some specific regulation, such as, for example, a heat shock response, or an adaptation to nutritional starvation. In such circumstances, a UAS must exist in the 5'-untranslated upstream region near the promoter sequence, and positive or negative regulatory proteins (i.e. trans-acting factors) must recognize and bind to the UAS. The binding strength of the transcription initiation complex to the promoter sequence is affected by the binding of the trans-acting factors around the promoter, and this enables the regulation of transcription activity.

After the activation of the transcription initiation complex by phosphorylation, the transcription initiation complex initiates transcription from the transcription start site. Some parts of the transcription initiation complex detach and form an elongation complex that separates from the promoter region and progresses in the 3'-direction of the gene (this step is called a promoter clearance event). The elongation complex continues transcription until it reaches a termination sequence located in the 3'-adjacent downstream region of the gene.

In order to decrease the expression of a gene of interest, conventional chemical mutagenesis or site-directed mutagenesis are often used to introduce mutations in the promoter region of a gene of interest containing a UAS sequence. In this approach, a gene cassette, containing a reporter gene fused to a promoter region derived from the gene of interest at its 5'-end and a terminator region from the gene of interest at its 3'-end, is mutagenized and then introduced into *P. rhodozyma*. By detecting variations in the activity of the reporter gene, effective mutations can be screened. Mutant strains in which the expression of an enzyme of interest might be decreased can be obtained by transforming a host strain with a recombinant DNA having such a mutated promoter region.

Vector constructs that contain an anti-sense AOX gene or a mutated promoter of an AOX gene can be transferred into an appropriate host strain. When *Phaffia rhodozyma* is used as a host strain, a vector that contains a selectable marker that functions in *P. rhodozyma* is used for cloning the mutant constructs. A drug resistance gene that encodes an enzyme that enables the host to survive in the presence of a toxic antibiotic is often used as a selectable marker. The G418 resistance gene harbored in pGB-Ph9 (Wery et al., Gene, 184, 89–97, 1997) is an example of a drug resistance gene. Such a plasmid can be integrated into the chromosome of *Phaffia rhodozyma* through homologous recombination between the chromosome and the plasmid.

The preferred methods for transforming *P. rhodozyma* are the LiAc and electroporation methods described by Wery et al., Gene, 184, 89–97, 1997.

A genetically engineered *P. rhodozyma*, as set forth above, would be cultivated in an appropriate medium and evaluated for its productivity of astaxanthin.

The following examples are provided to further illustrate methods of preparation of the compositions of the present invention, as well as certain physical properties and uses thereof. These examples are illustrative only and are not intended to limit the scope of the invention in any way.

EXAMPLES

The following materials and methods were employed in the examples described below:

Strains
  *P. rhodozyma* ATCC 96594 (re-deposited under the accession No. ATCC 74438 on Apr. 8, 1998 pursuant to the Budapest Treaty)
  *E. coli* Y1090r$^-$: araD139, hsdR ($r_K^-$, $m_K^+$), mcrB$^+$, rpsL, supF, trpC12::Tn10, ΔlacU169, Δlon, F$^-$, λ$^-$, (pMC9) (Clontech)
  *E. coli* DH5alpha: F$^-$, 100 80d, lacZΔM15, Δ(lacZYA-argF)U169, hsd ($r_K^-$, $m_K^+$), recA1, endA1, deoR, thi-1, gyrA96, relA1 (Toyobo, Osaka, Japan)
  *E. coli* gamma delta donor: Δ(gpt-proA)62, leu, 44, ara14, galK2, lacY1, Δ(mcrC-mrr), ($r_{rB}^-$, $m_B^-$), xyl-5, mtl-1, recA13, [F$^+$:: Tn10000 (tet$^s$)] (Novagene)
  *E. coli* gamma delta recipient: F$^-$, araD139, Δ(ara-leu)7696, gal/E15, galK16, Δ(lac)X74, (Str$^r$), hsdR2 ($r_{K12}^-$, $m_{K12}^+$), mcrA, mcrB1::Tn5 (kan$^r$) (Novagene)
  *E. coli* TOP10: F$^-$, mcrA, Δ(mrr-hsdRMS-mcrBC), φ80, M15, ΔlacX74, recA1, deoR, araD139, (ara-leu)7697, galU, galK, rpsL (Str$^r$), endA1, nupG (Invitrogen, NV Leek, the Netherlands)

Vectors
  lambda gt11 (Clontech)
  pCR2.1-TOPO (Invitrogen)
  pOCUS-2
  pBluescript II SK-(Stratagene)
  pGBPh9 (Wery et al., Yeast, 12, 641–651, 1996)

Media

P. rhodozyma was maintained in YPD medium (DIFCO, Detroit, U.S.A.). E. coli was maintained in LB medium (10 g Bacto-tryptone (DIFCO), 5 g yeast extract (DIFCO) and 5 g NaCl per liter). NZY medium (5 g NaCl, 2 g $MgSO_4$-$7H_2O$, 5 g yeast extract (DIFCO), 10 g NZ amine type A (WAKO, Osaka, Japan) per liter) was used for lambda phage propagation in soft agar (0.7% agar; WAKO). When agar medium was prepared, 1.5% of agar (WAKO) was supplemented. Salicylhydroxamic acid (SHAM) was purchased from Aldrich (Milwaukee, U.S.A.).

Methods

General methods of molecular genetics were practiced according to Molecular Cloning: A Laboratory Manual, 2nd Edition, Cold Spring Harbor Laboratory Press, 1989.

Restriction enzymes and T4 DNA ligase were purchased from Takara Shuzo (Ohtsu, Japan).

Chromosomal DNA from P. rhodozyma was isolated using a QIAGEN Genomic Kit (QIAGEN, Hilden, Germany) following the protocol supplied by the manufacturer. Plasmid mini-prep DNA from transformed E. coli was isolated using the Automatic DNA isolation system (PI-50, Kurabo, Co. Ltd., Osaka, Japan). Plasmid midi-prep DNA from transformed E. coli was isolated using a QIAGEN column (QIAGEN). DNA fragments were isolated and purified from agarose using QlAquick or QIAEX II (QIAGEN).

Total RNA from P. rhodozyma was isolated using the Isogen phenol method. (Nippon Gene, Toyama, Japan). mRNA was purified from total RNA using an mRNA separation kit (Clontech). cDNA was synthesized using the CapFinder CDNA construction kit (Clontech).

In vitro packaging was performed using Gigapack III gold packaging extract (Stratagene, La Jolla, U.S.A.). Isolation of lambda DNA was performed using the Wizard lambda preps DNA purification system (Promega, Madison, U.S.A.) and following the protocol prepared by the manufacturer.

Polymerase chain reaction (PCR) was performed with the thermal cycler from Perkin Elmer, model 2400. PCR conditions are described in the examples. PCR primers were purchased from a commercial supplier. DNA sequencing was performed with an automated fluorescent DNA sequencer (ALFred, Pharmacia).

Competent cells of DH5alpha were purchased from Toyobo. All of the chemicals were purchased from WAKO, unless otherwise stated.

The following examples are provided to further illustrate the process of the present invention. These examples are illustrative only and are not intended to limit the scope of the invention in any way.

Example 1

Isolation of SHAM-Resistant Mutants, SHAM1, SHAM2, and SHAM3 from P. Rhodozyma ATCC 96594

To examine the effects of the inhibition of KCN-resistant respiration mediated by alternative oxidase on the growth of P. rhodozyma, SHAM was added to a culture of P. rhodozyma on YPD-agar medium. SHAM was dissolved in ethanol and added to the YPD-agar medium to give 0.05, 0.15, 0.30, 0.45 and 0.90 mg/ml as a final concentration. After dilution, $2 \times 10^7$ cells/ml of P. rhodozyma ATCC 96594 were spread on the media. After a 3 day-cultivation at 20° C., colonies were counted. The number of colonies that grew on SHAM-containing YPD agar was almost the same as that on control medium which did not contain SHAM. However, the colonies that grew on SHAM-containing media were smaller than the colonies that grew on the control media. TABLE 1 shows the diameter of colonies that grew on SHAM-containing media relative to the size of control colonies.

TABLE 1

| Relative size of colonies that grew on SHAM-containing YPD-agar | | | | | |
|---|---|---|---|---|---|
| SHAM (mg/ml) | 0.05 | 0.15 | 0.30 | 0.45 | 0.90 |
| Relative colony diameter (%) | 100 | 70 | 40 | 30 | 12 |

Among the colonies that grew on media containing 0.3 and 0.45 mg/ml of SHAM, some colonies were of a similar size relative to the control colonies. Such colonies also showed deeper pigmentation than the controls. Four colonies, which showed similar colony size to the controls, were picked and streaked onto YPD-agar medium. All of the colonies showed deeper pigmentation than the controls, even on YPD-agar medium that did not contain SHAM. These results suggest that these strains might be spontaneous mutants. The strains were designated SHAM1, SHAM2, SHAM3, and SHAM4.

Example 2

Flask Fermentation of Resistant Mutants, SHAM1, SHAM2 and SHAM3

To evaluate the productivity of astaxanthin by the SHAM-resistant mutants, SHAM1, SHAM2 and SHAM3, the mutants were grown by fermentation in shaking flasks. These mutants and their parent strain, ATCC 96594, were inoculated from freshly prepared agar-culture into 50 ml of YPD medium in a 500 ml baffle flask at a final OD (optical density) at 660 nm of 0.05. Fermentation was carried out at 20° C. at 200 r.p.m. At appropriate intervals, 3 ml of broth were withdrawn and analyzed for cell yield and astaxanthin content.

Cell yield was measured as OD at 660 nm. Dry cell weight was measured by weighing cells derived from 1.0 ml of broth after heating at 120° C. overnight in a 1.5 ml microcentrifugation tube. The astaxanthin content of P. rhodozyma was measured by HPLC after the extraction of carotenoids from cells of P. rhodozyma by disruption with glass beads, as follows. Cells obtained from 1 ml of broth after the centrifugation were concentrated two-fold with distilled water and 10.0 grams of glass beads were added to the cell suspension (0.5 ml) in a brown-shaded test tube (13.5 mm, 11 cm). Next, 1.5 ml of acetone/butylated hydroxy toluene (BHT)/water (45 mg of BHT in 450 ml acetone and 50 ml water) were added and the test tube was shaken with a horizontal table top shaker for an hour. After extraction, 5 ml of acetone/BHT/water, containing an appropriate concentration of bixin (nacalai tesque, Kyoto, Japan) as an internal standard, were added. The supernatant was analyzed for astaxanthin content using the following HPLC system (the hardware for the HPLC system was purchased from Tosoh (Tokyo, Japan):

HPLC column: YMC-Pak ODS-A (6 mm, 150 mm (YMC, Inc., Milford, U.S.A.)).

Temperature: room temperature

Eluent: acetonitrile/methanol/isopropanol (85/10/5)

Injection volume: 10 microliters

Flow Rate: 2.0 ml/minute

Detection: UV at 471 nm

The results are summarized in TABLE 2. All of the mutants showed 50% higher productivity of astaxanthin than the parent strain, ATCC 96594. These results suggest that some mutations might occur in these mutants in order to compensate for the inhibition of alternative oxidase activity by increasing astaxanthin production.

TABLE 2

Productivity of astaxanthin by SHAM-resistant mutants

| | astaxanthin productivity | | | | | |
|---|---|---|---|---|---|---|
| | (mg/L) | | (mg/g-dried cell) | | OD@660 nm | |
| (hours) | 38 | 72 | 38 | 72 | 38 | 72 |
| SHAM-1 | 1.65 | 4.07 | 0.179 | 0.380 | 24.5 | 30.6 |
| SHAM-2 | 2.36 | 4.43 | 0.217 | 0.385 | 29.5 | 30.5 |
| SHAM-3 | 2.87 | 3.97 | 0.247 | 0.381 | 29.2 | 29.5 |
| ATCC 96594 | 2.00 | 2.76 | 0.164 | 0.258 | 27.4 | 28.7 |

Example 3

Isolation of mRNA From *P. Rhodozyma* and Construction of a cDNA Library

In order to construct a cDNA library of *P. rhodozyma*, total RNA was isolated using the phenol extraction method immediately after cell disruption, and the mRNA from the *P. rhodozyma* ATCC 96594 strain was purified using an mRNA separation kit (Clontech).

Cells of the ATCC 96594 strain continued in 10 ml of a two-day-culture in YPD medium were harvested by centrifugation (1500× g for 10 minutes) and washed once with extraction buffer (10 mM Na-citrate/HCl (pH 6.2) containing 0.7 M KCl). After suspending in 2.5 ml of extraction buffer, the cells were disrupted using a French press homogenizer (Ohtake Works Corp., Tokyo, Japan) at 1500 kgf/cm$^2$, and immediately mixed with two volumes of isogen (Nippon gene) according to the method specified by the manufacturer. 400 micrograms of total RNA were recovered.

Total RNA was purified using an mRNA separation kit (Clontech) according to the method specified by the manufacturer. 16 micrograms of mRNA from the *P. rhodozyma* ATCC 96594 strain were obtained.

To construct a cDNA library, a CapFinder PCR cDNA construction kit (Clontech) was used according to the method specified by the manufacturer. One microgram of purified mRNA was applied for first strand synthesis, followed by PCR amplification. After PCR amplification, 1 mg of cDNA was obtained.

Example 4

Cloning of a Partial AOX (Alternative Oxidase) Gene from *P. Rhodozyma*

To clone a partial AOX gene from *P. rhodozyma*, the degenerate PCR method was used. The alternative oxidase sequences used for multiple alignment analysis (Clustal W., Thompson J. D., et al., Nucleic Acids Research, 22, 4673–4680, 1994) were obtained from the indicated database using the following species designation and accession numbers:

| | |
|---|---|
| *Aspergillus niger* | AB016540 (DDBJ/GenBank/EMBL) |
| *Candida albicans* | AF031229 (DDBJ/GenBank/EMBL) |

-continued

| | |
|---|---|
| *Chlamydomonas reinhardtii* | AF047832 (DDBJ/GenBank/EMBL) |
| *Magnaporthe grisea* | AB005144 (DDBJ/GenBank/EMBL) |
| *Neurospora crassa* | Q01355 (Swissprot) |
| *Oryza sativa* | AB004813 (DDBJ/GenBank/EMBL) |
| *Pichia anomala* | Q00912 (Swissprot) |
| *Trypanosoma brucei brucei* | Q26710 (Swissprot) |

Based on the common sequence of known alternative oxidase genes from other species, two mixed primers were designed and synthesized with the nucleotide sequences shown in Table 3.

TABLE 3

Sequence of primers used in the cloning of the AOX gene aox3: AAYGARMGNATGCAYYTNYTNACNTT (SEQ ID NO: 3)
(sense primer)

aox5: GCYTCYTCYTCNARRTANCCNACRAA (SEQ ID NO: 4)
(antisense primer)

(N=A, C, G or T; R=A or G, Y=C or T, M=A or C)

After a PCR reaction of 25 cycles at 95° C. for 30 seconds, 50° C. for 30 seconds and 72° C. for 15 seconds, using ExTaq (Takara Shuzo) as a DNA polymerase and the cDNA pool obtained in Example 1 as a template, the reaction mixture was applied to an agarose gel and electrophoresis was carried out. A PCR band of the desired length was recovered and purified by QIAquick (QIAGEN) according to the method supplied by the manufacturer, and ligated to pCR2.1-TOPO (Invitrogen). After the transformation of competent *E. coli* TOP10, 6 white colonies were selected and plasmid DNA was isolated using the Automatic DNA isolation system. As a result of sequencing, it was found that 3 clones had a sequence whose deduced amino acid sequence was similar to known alternative oxidase genes. One of the isolated cDNA clones was designated as pAOX5 14 and used for further study.

Example 5

Isolation of Genomic DNA From *P. Rhodozyma*

To isolate genomic DNA from *P. rhodozyma*, a QIAGEN genomic kit was used according to the method specified by the manufacturer.

Cells of the *P. rhodozyma* ATCC 96594 strain from 100 ml of overnight culture in YPD medium were harvested by centrifugation (1500× g for 10 minutes) and washed once with TE buffer (10 mM Tris/HCl (pH 8.0) containing 1 mM EDTA). After suspending in 8 ml of Y1 buffer from the QIAGEN genomic kit, lyticase (SIGMA, St. Louis, U.S.A.) was added at a concentration of 2 mg/ml to disrupt the cells by enzymatic degradation. The reaction mixture was incubated for 90 minutes at 30° C. before proceeding to the next extraction step. Finally, 20 micrograms of genomic DNA were obtained.

Example 6

Southern Blot Hybridization Using pAOX514 As a Probe

Southern blot hybridization was used to clone a genomic fragment that contains the AOX gene from *P. rhodozyma*. Two micrograms of genomic DNA were digested with EcoRI and subjected to agarose gel electrophoresis followed by acidic and alkaline treatment. The denatured DNA was transferred onto a nylon membrane (Hybond N+, Amersham, Buckinghamshire, U.K.) using a transblot (Joto Rika, Tokyo, Japan) for one hour. The DNA that was transferred onto the nylon membrane was fixed by heat treatment (80° C., 90 minutes). A probe was prepared by labeling template DNA (EcoRI-digested pAOX514) with the DIG multipriming method (Boehringer Mannheim). Hybridization was performed by the method specified by the manufacturer. As a result, a hybridized band was visualized in the range from 5.5 to 7.0 kilobases (kb).

Example 7

Cloning of a Genomic Fragment Containing the AOX Gene

Four micrograms of genomic DNA were digested with EcoRI and subjected to agarose gel electrophoresis. Then, DNA fragments whose length was within the range from 5.0 to 7.0 kb were recovered by QIAEX II gel extraction kit (QIAGEN) according to the method specified by the manufacturer. The purified DNA was ligated to 0.5 micrograms of EcoRI-digested and CIAP (calf intestine alkaline phosphatase)-treated lambda gt11 (Clontech) at 16° C. overnight, and packaged using Gigapack III gold packaging extract (Stratagene). The packaged extract was inoculated onto the E. coli Y1090 strain, and over-laid with NZY medium poured onto the LB agar medium. About 6000 plaques were screened using EcoRI-digested pAOX514 as a probe. One plaque hybridized to the labeled probe.

The lambda gt11 derivative containing the putative AOX gene from P. rhodozyma was prepared using the Wizard lambda preps DNA purification system (Promega). As a result of digestion with EcoRI, it was revealed that this lambda gt11 derivative contained a 6 kb EcoRI insert. Next, PCR was carried out using this lambda gt11 derivative as a template and the aox3 and aox5 primers. PCR using the same PCR conditions described in Example 4 yielded the expected 0.3 kb band. These results suggested that this lambda gt11 derivative contains the putative AOX gene from P. rhodozyma. A 6.0 kb insert EcoRI fragment from this lambda gt11 derivative was purified using QIAquick (QIAGEN) and subcloned into the pOCUS-2 vector (Novagen) using DH5alpha as a host strain. The resulting plasmid was named pOCUSAOX607.

Example 8

Sequencing of the Genomic Fragment Containing the AOX Gene pOCUSAOX607 was transferred into competent gamma delta donor cells and used for the preparation of sequencing derivatives which were used for the Locus Pocus system (Novagen). Sequencing derivatives were prepared according to the protocol supplied by the manufacturer. Cy5-labelled sequencing primers, whose sequences are listed in TABLE 4, were synthesized and used for sequencing using the AutoCycle sequencing kit (Pharmacia).

TABLE 4

Sequence of primers used for sequencing the AOX gene

| | |
|---|---|
| poc1: (Cy5-) AGCTACAACATACGAAAGGG | (SEQ ID NO: 5) |
| poc2: (Cy5-) GGGGAACTGAGAGCTCTAAA | (SEQ ID NO: 6) |

As a result of sequencing, a 2561 base pair nucleotide sequence of the genomic fragment containing the AOX gene from P. rhodozyma was determined.

The coding region was 1206 base pairs long and consisted of 10 axons and 9 introns. Introns were dispersed all throughout the coding region, without 5'or 3'bias. By using genetic analysis software, GENETYX-SV/RC (Software Development Co., Ltd., Tokyo, Japan) version 4.0.1, it was determined that the open reading frame consists of 402 amino acids (SEQ ID NO: 1), whose sequence is strikingly similar to the known amino acid sequences of alternative oxidases from other species (e.g. 51.5% identity to the alternative oxidase from *Aspergillus niger*). A stretch of hydrophobic amino acid residues located at the amino terminal end, which was expected to form an alpha-helix structure, indicated that this amino terminal region might be a membrane spanning domain or a transit peptide for mitochondria. The PSORTII program predicted that this protein might be a mitochondrial protein at an 82.6% prediction value.

Example 9

Cloning of the Upstream Region of the AOX Gene

Cloning of the 5'-adjacent region of the AOX gene was performed using the Genome Walker Kit (Clontech) because it seemed that pAOX514 might not have sufficient length to contain a promoter for the AOX gene. The PCR primers, whose sequences are set forth in TABLE 5, were synthesized.

TABLE 5

Sequence of the primers used in the cloning of 5'- adjacent region of the AOX gene

| | |
|---|---|
| aox13: GTGTCAGAAACCTCAGATCAACAGGC (primary primer) | (SEQ ID NO: 7) |
| aox14: CAACAGGCAGTACAGTCAGCAGATTC (nested primer) | (SEQ ID NO: 8) |

Protocols used for library construction and PCR conditions were the same as those specified by the manufacturer. The genomic DNA preparation obtained in Example 5 was used as a PCR template. The PCR fragments that had a ScaI site at the 5'- end (1.2 kb), and that had a DraI site at the 5'-end (3.0 kb), were recovered and cloned into pCR2.1-TOPO by using E. coli TOP10 as a host strain. As a result of sequencing 2 independent clones from each of the two constructs, it was confirmed that the 5'-adjacent region of the AOX gene was cloned. The clone obtained in the above experiment was designated as pAOXSc702 and was used for further study. Based on the sequence of the insert fragment in pAOXSc702, 4 PCR primers, whose sequence are listed in TABLE 6, were synthesized.

TABLE 6

Sequence of primers used for cloning the AOX promoter region

| | | |
|---|---|---|
| aox15: | GAATTCAACAGGTCAAATGA (sense primer) | (SEQ ID NO: 9) |
| aox16: | ATCCACCCACGCCTGTTTCC (antisense primer) | (SEQ ID NO: 10) |
| aox17: | GGAAACAGGCGTGGGTGGAT (sense primer) | (SEQ ID NO: 11) |
| aox18: | GAATTCAGTAAACGCATTAG (antisense primer) | (SEQ ID NO: 12) |

The PCR conditions used were the same as those used in Example 4, except that HF polymerase (Clontech) was used as a DNA polymerase. Using the combination of aox15 and aox16, a 0.7 kb fragment was amplified. Using the combination of aox17 and aox18, a 0.5 kb fragment was amplified. These fragments were cloned into pCR2.1-TOPO and transformed into *E. coli* TOP10. Plasmids were prepared from 6 independent white colonies and subjected to sequencing. Expected clones with identical insert fragment sequences were obtained. The clone obtained using the combination of aox15 and aox16 was named pAOX714 #1516. The clone obtained using the combination of aox17 and aox18 was named pAOX714 #1718. As a result of sequencing, the sequences of pAOX714 #1516 and pAOX714 #1718, which contained the promoter region for the AOX gene from *P. rhodozyma*, were determined. The determined sequences containing the AOX promoter were 1406 base pairs in length.

Combining the sequences obtained in Examples 8 and 9, the nucleotide sequence (3.7 kb) (SEQ ID NO: 2) of the AOX gene, and its promoter and terminator, was determined.

Example 10

Construction of an Antisense Plasmid for the AOX Gene

An antisense gene fragment that covered the entire structural AOX gene was amplified using PCR as set forth below. The fragment was then cloned into an integration vector from which the antisense AOX gene was transcribed by an AST promoter in *P. rhodozyma*.

TABLE 7

Sequence of the primers used in the
antisense construction of the AOX gene aox101:
GGCCATTATGGCCTCAATTGGTCTGAGACATGC    (SEQ ID NO: 13)

aox102:
GGCCGAGGCGGCCATGTCTCTTGCTAGATGTCT    (SEQ ID NO: 14)

Both primers, aox101 and aox102, have asymmetrical recognition sequences for the restriction enzyme SfiI (GGCCNNNNNGGCC), however, their asymmetrical hang-over sequences were designed to be different. This might enable directional cloning into expression vectors which have the equivalent asymmetrical sequences at their ligation sequences.

PCR was performed using HF polymerase (Clontech) and the cDNAs prepared in Example 3 as a template, under the following conditions: 30 cycles at 94° C. for 15 seconds, 55° C. for 30 seconds and 72° C. for 45 seconds. The amplified PCR fragment was purified and cloned into the pCR2.1-TOPO vector. As a result of sequencing, it was determined that one of the clones had the correct fragment, and this clone was named pAOX1007 #0102. The sequence of antisense fragment for AOX gene is listed in SEQ ID NO: 15.

In order to provide promoter and terminator fragments that drive the transcription of the antisense AOX gene, the AST promoter and terminator were cloned from the chromosomal DNA prepared in Example 5.

TABLE 8

Sequence of primers used for the cloning
of the AST promoter and terminator

| | | | |
|---|---|---|---|
| ast49: | GCGGCCGCACGTACAGACTAAGATCGAC | (sense primer) | (SEQ ID NO: 16) |
| ast50: | GGCCATAATGGCCATGGAGAAAGTAGGTGGCAA | (antisense primer) | (SEQ ID NO: 17) |
| ast36: | CCTGCAGGCCGCCTCGGCCGTTGATTCTTCATATGTTAA | (sense primer) | (SEQ ID NO: 18) |
| ast37: | GGTACCCTGCAGTCGACAAACATGAA | (antisense primer) | (SEQ ID NO: 19) |

The PCR conditions used were as follows: 25 cycles at 94° C. for 15 seconds, 55° C. for 30 seconds and 72° C. for 90 seconds. The combination of ast49 and ast50 amplified a 1.25 kb fragment. The combination of ast36 and ast37 amplified a 0.3 kb fragment. These fragments were cloned into pC2.1-TOPO and used to transform *E. coli* TOP10. Plasmids were prepared from 6 independent white colonies and subjected to sequencing. As a result, the clones that had the correct sequences of the AST promoter and terminator (European Patent Application No. 1 035 206 A1) were selected for further study (pUAST407 for the AST promoter and pAST526 #3637 for the AST terminator).

The AST terminator sequence was fused to a G418 resistant cassette by ligating NotI- and KpnI-digested pAST526 #3637, and KpnI- SacI-digested pG418Sa330 (European Patent Application No. 1 035 206 A1), to NotI- and SacI- digested pBluescriptII SK-(Stratagene). The ligation mixture was transformed into competent KB822 cells. As a result of restriction analysis, one clone (pUAST418), which had the correct structure, was selected for further study.

A 3.1 kb SacI fragment containing the ribosomal DNA (rDNA) locus (Wery et al., Gene, 184, 89–97, 1997) was inserted downstream of the G418 cassette of pUAST418. rDNA fragments exist in multicopies on the chromosome of eukaryotes. An integration event at the rDNA fragment results in multicopy integration onto the chromosome of the host, thus, enabling overexpression of foreign genes harbored in the expression vector. For this purpose, a SacI fragment from pGBPh9 containing the rDNA gene was ligated to a SacI-digested and bacterial alkaline phosphatase-treated pUAST418. The ligation mixture was transformed into competent KB822 cells. As a result of restriction enzyme analysis, two clones, in which the rDNA fragment was inserted in different orientations, were selected for further study (pURDNA421 and pURDNAR421).

The AST promoter was inserted upstream of the AST terminator to construct an expression vector which functions in *P. rhodozyma*. A 1.0 kb NotI-BglII fragment of pUAST407, and a 0.25 kb BglII- PstI fragment of pUAST407, were ligated to NotI- and Sse8387I-digested pURDNA421 or pURDNAR421. Competent KB822 cells were transformed by the ligation mixture and 6 resultant colonies were subjected to restriction analysis. Clones which had the correct insertion of the AST promoter were selected for further study. Two clones were selected and designated pF718 and pR718, each plasmid having the opposite orientation of the rDNA fragment relative to each other.

The antisense AOX constructs were completed by inserting a 1.2 kb SfiI fragment of pAOX1007 #0102 into SfiI-digested pF718 or pR718. The resultant plasmids were named pFAOX828 and pRAOX828.

Example 11

Transformation of P. Rhodozyma With the AOX-Antisense Plasmids

The AOX-antisense vectors, pFAOX828 and pRAOX828, were transformed into the P. rhodozyma wild type strain, ATCC 96594. Biolistic transformation was performed according to the method described in Methods in Molecular Biology (Johnson et al., 53, 147–153, 1996). The P. rhodozyma strain, ATCC 96594, was cultured in YPD medium to stationary phase. After centrifugation of the culture, cells were concentrated 10-fold with sterilized water. 200 microliters of the cell suspension were spread on YPD medium containing 100 micrograms/ml of geneticin and 0.75M of D-mannitol and D-sorbitol. Five micrograms of plasmid DNA were coated on 1.5 mg of 0.9 micrometer gold particles, and used as donor DNA for Biolistic transformation. One geneticin resistant colony that was transformed with pFAOX828, and showed enhanced pigmentation, was selected for further characterization in view of its increased astaxanthin productivity and its decreased activity of alternative oxidase, which was encoded by the AOX gene.

Example 12

Characterization of the pFAOX828 Integrant Derived from P. Rhodozyma, ATCC 96594

The P. rhodozyma transformant, ATCC 96594::pFAOX828, and its parent strain ATCC 96594, were separately cultured in 50 ml of YPD medium in a 500 ml Erlenmeyer flask at 20° C. for 3 days using a seed culture that grew in 10 ml of YPD medium in test tubes (21 mm in diameter) at 20° C. for 3 days. At different time points, e.g., at 24, 43, and 65 hours after the inoculation, appropriate volume of culture broth were withdrawn and used for analyzing growth, astaxanthin productivity, and oxygen uptake activity, under the presence or absence of KCN. The 24, 43, and 65 hour-time points correspond to late the log-phase, mid-stationary, and late stationary phases of growth, respectively.

In order to monitor growth, the optical density at 660 $\mu$m was measured using a UV-1200 photometer (Shimadzu Corp., Kyoto, Japan). In addition, dried cell mass was measured by drying cells, derived from 1 ml of broth after microcentrifugation, at 100° C. for one day.

In order to measure astaxanthin content and total carotenoid content, cells were harvested from 1.0 ml of broth after microcentrifugation and used for the extraction of carotenoids by disruption with glass beads. After extraction, disrupted cells were removed by centrifugation and the supernatant was analyzed for carotenoid content using HPLC. The HPLC conditions used were as follow:

HPLC column: Chrompack Lichrosorb si-60 (4.6 mm, 250 mm)

Temperature: room temperature

Eluent: acetone/hexane (18/82), add 1 ml/L of water to eluent

Injection volume: 10 microliters

Flow rate: 2.0 ml/minute

Detection: UV at 450 nm

A reference sample of astaxanthin was obtained from F. Hoffmann-La Roche AG (Basel, Switzerland).

To measure respiration activity, by measuring oxygen uptake activity in the presence or absence of KCN, a DO meter, model B-505, and a DO probe, GU-BM, manufactured by Iijima Electronics Corporation (Aichi, Japan), were used. Harvested cells were resuspended in 0.5 M KPB (pH 7.4). 200 microliters of this cell suspension were diluted with 2.3 ml of water in the chamber of the DO analyzer. The measurement was initiated by the addition of 0.2 ml of 1M glucose in the presence or absence of 0.48 mM KCN. Results are summarized in Table 9.

TABLE 9

| | strain | | | | | |
|---|---|---|---|---|---|---|
| | ATCC 96594 :: pFAOX828 | | | ATCC 96594 | | |
| | time (hours) | | | | | |
| | 24 | 43 | 65 | 24 | 43 | 65 |
| OD at 660 nm | 22.75 | 28.26 | 27.91 | 28.75 | 31.707 | 31.10 |
| dried cells (mg/ml) | 10.8 | 12.7 | 12.3 | 11.6 | 12.1 | 11.6 |
| astaxanthin (mg/g-dried cells) | 0.090 | 0.223 | 0.240 | 0.107 | 0.194 | 0.211 |
| carotenoids (mg/g-dried cells) | 0.218 | 0.336 | 0.354 | 0.213 | 0.269 | 0.288 |
| respiration | | | | | | |
| KCN- sensitive | 11.29 | 5.84 | 4.02 | 16.03 | 6.13 | 4.96 |
| KCN- resistant | 0.29 | 0 | 0 | 1.48 | 0.78 | 0.15 |

(Respiration activity is expressed as nmol $O_2$-uptake/minutes x mg-dried cells.)

As shown in Table 9, antisense AOX transformant ATCC 96594 :: pFAOX828 showed a cell yield similar to the parent strain, ATCC 96594 at 43 hours, although it showed slower growth at 24 hours. The astaxanthin and carotenoid content of the transformant increased by about 15% at 43 hours compared to the parent strain. The transformant showed similar KCN-sensitive respiration activity compared to the host strain (95%). However, the KCN-resistant respiration, which is mediated by alternative oxidase of the transformant, decreased to 20% of the levels of the host strain at 24 hours, and was completely impaired at 43 hours.

These results suggest that the decrease in alternative oxidase activity, which mediated KCN-resistant respiration, may lead to the overproduction of astaxanthin and carotenoids in P. rhodozyma.

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for producing an enhanced carotenoid-producing microorganism comprising:
   (a) selecting a parental microorganism that produces a carotenoid and that comprises a polynucleotide sequence encoding a polypeptide having alternative oxidase (AOX) activity selected from the group consisting of SEQ ID NO: 2, a fragment of SEQ ID NO: 2, and a polynucleotide that hybridizes to the complement of SEQ ID NO: 2 under the following conditions: hybridization in 6X SSC, 0.5% SOS, 100 micrograms/ml denatured salmon sperm DNA, 50% formamide overnight at 42° C. followed by a wash in 2X SSC, 0.5% SDS at room temperature for 15 minutes and a subsequent wash in 0.1X SSC, 0.5% SDS at room temperature for 15 minutes;
   (b) altering said polynucleotide sequence in the parental microorganism to form a mutant microorganism, which mutant has a reduced level of AOX enzymatic activity compared to the parental microorganism; and
   (c) selecting a mutant microorganism that produces at least 10% more of the carotenoid compared to the parental microorganism.

2. A process according to claim 1 wherein the altering step comprises a technique selected from the group consisting of introducing into said microorganism a plasmid that produces an antisense strand complementary to said polynucleotide in the microorganism and site-directed mutagenesis.

3. A process according to claim 1 wherein the parental microorganism is a Protista or a Fungi.

4. A process according to claim 3 wherein the parental microorganism is a member of a genus selected from the group consisting of Synechococcus, Synechocystis, Haematococcus, Dunaliella, Phaffia, Xanthophyllomyces, Neurospora, Rhodotorula, Blakeslea, and Phycomyces.

5. A process according to claim 4 wherein the parental microorganism is a strain of Phaffia rhodozyme.

6. A process according to claim 5 wherein the parental microorganism is a strain selected from the group consisting of DSM 13429, 13430, and 13431.

7. An enhanced carotenoid-producing mutant microorganism produced from a parental carotenoid-producing microorganism comprising a polynucleotide sequence encodinq a polypeptide having alternative oxidase AOX activity selected from the group consisting of SEQ ID NO: 2, a fragment of SEQ ID NO: 2, and a ploynucleotide that hybridizes to the complement of SEQ ID NO: 2 under the following conditions: hybridization in 6X SSC, 0.5% SDS, 100 micrograms/ml denatured salmon sperm DNA, 50% formamide overnight at 42° C. followed by a wash in 2X SSC, 0.5% SDS at room temperature for 15 minutes and a subsequent wash in 0.1X SSC, 0.5% SDS at room temperature for 15 minutes, wherein the level of AOX enzymatic activity in the mutant is reduced compared to the parental microorganism and the mutant produces at least 10% more of a carotenoid compared to the parental microorganism.

8. An enhanced carotenoid-producing mutant microorganism according to claim 7 wherein the expression of AOX is altered with a technique selected from the group consisting of complementary to said polynucleotide in the microorganism and site-directed mutagenesis.

9. An enhanced carotenoid-producing mutant microorganism according to claim 7 wherein the parental microorganism is a Protista or a Fungi.

10. An enhanced carotenoid-producing mutant microorganism according to claim 9 wherein the parental microorganism is a member of a genus selected from the group consisting of Synechococcus, Synechocystis, Haematococcus, Dunaliella, phaffia, Xanthophyllomyces, Neurospora, Rhodotorula, Blakeslea, and Phycomyces.

11. An enhanced carotenoid-producing mutant microorganism according to claim 10 wherein the parental microorganism is *Phaffia rhodozyma*.

12. An enhanced carotenoid-producing mutant microorganism according to claim 11 wherein the parental microorganism is a strain selected from the group consisting of DSM 13429, 13430, and 13431.

13. An isolated polynucleotide comprising a polynucleotide sequence encoding a polypeptide having alternative oxidase (AOX) activity selected from the group consisting of SEQ ID NO: 2, a fragment of SEQ ID NO: 2 , and a polynucleotide that hybridizes to the complement of SEQ ID NO: 2 under the following conditions: hybridization in 6X SSC, 0.5% SDS, 100 micrograms/ml denatured salmon sperm DNA, 50% formamide overnight at 42° C. followed by a wash In 2X SSC, 0.5% SDS at room temperature for 15 minutes and a subsequent-wash in 0.1X SSC, 0.5% SDS at room temperature for 15 minutes.

14. An isolated polynucleotide according to claim 13 wherein the polynucleotide sequence is derived from a carotenoid-producing microorganism.

15. An isolated polynucleotide according to claim 14 wherein the microorganism is a Protista or a Fungi.

16. An isolated polynucleotide according to claim 15 wherein the microorganism is a member of a genus selected from the group consisting of Synechococcus, Synechocystis, Haematococcus, Dunaliella, Phaffia, Xanthophyllomyces, Neurospora, Rhodotorula, Blakeslea, and Phycomyces.

17. An isolated polynucleotide according to claim 16 wherein the microorganism is *Phaffia rhodozyma*.

18. An isolated polynucleotide according to claim 13, comprising SEQ ID NO: 2 or a fragment of SEQ ID NO: 2 encoding a polypeptide having AOX activity.

19. An isolated polynucleotide according to claim 13 comprising SEQ ID NO; 2 or a polynucleotide sequence having a sequence identity of more than 95% with SEQ ID NO:2.

20. An isolated polynucleotide according to claim 13 comprising SEQ ID NO: 2.

21. An isolated polynucleotide which encodes an amino acid sequence of SEQ ID NO: 1 or a fragment of SEQ ID NO: 1 having AOX.

* * * * *

SEQUENCE LISTING

<160> NUMBER OF SEQ ID NOS: 19

<210> SEQ ID NO 1
<211> LENGTH: 401
<212> TYPE: PRT
<213> ORGANISM: Phaffia rhodozyma

<400> SEQUENCE: 1

```
Met Ser Leu Ala Arg Cys Leu Val Gln Ala Ser Thr Arg Ser Leu Ser
  1               5                  10                  15

Arg Thr Val Arg Pro Ser Tyr Leu Thr Pro Leu Thr Val His Phe Phe
             20                  25                  30

Ser Ser Thr Ile Ser Arg Ser Cys Ser Arg Ser Tyr Ser Thr Ser Asn
         35                  40                  45

Thr Arg Leu Ser Thr Ser Asn Gly Gln Gln Ser Thr His His Leu Ala
     50                  55                  60

Asp Asn Val Pro Leu Thr Thr Asp Lys Gln Arg His Leu Gln Gly Val
 65                  70                  75                  80

Ile Gly Gly Glu Gly Met His Gln His Asp Ala Thr Val Ala His
                 85                  90                  95

Thr Asp Pro Leu Ala Ser Val Ile Gln Asp Leu Thr Val Pro Thr Asn
            100                 105                 110

Gly Ser Trp Val Met His Asn Pro Val Tyr Thr Arg Thr Glu Leu Asp
        115                 120                 125

Ala Val Gln Val Val His Arg Pro Pro Thr Asn Thr Ser Asp Gln Val
    130                 135                 140

Ser Thr Lys Leu Val Lys Met Leu Arg Trp Gly Phe Asp Leu Val Ser
145                 150                 155                 160

Asn Tyr Lys His Val Pro Phe Pro Ala Asn His Lys Glu Leu Ser Val
                165                 170                 175

Thr Gln Leu Arg Gln Met Gly Cys Leu Leu Ser Pro Asp Gln Trp Met
            180                 185                 190

Thr Arg Phe Ile Phe Leu Glu Thr Thr Ala Ala Ile Pro Gly Met Val
        195                 200                 205

Gly Gly Leu Leu Arg His Leu Gln Ser Leu Arg Leu Met Arg Arg Asp
    210                 215                 220

Gly Gly Trp Ile His Thr Leu Leu Ala Glu Ala Glu Asn Glu Arg Leu
225                 230                 235                 240

His Leu Leu Thr Phe Met Ser Met Ala Asn Pro Pro Leu Trp Phe Arg
                245                 250                 255

Ala Leu Ile Leu Gly Ala Gln Gly Val Phe Tyr Asn Leu Phe Phe Ile
            260                 265                 270

Thr Tyr Leu Ile Ser Pro Pro Val Ala His Arg Phe Val Ala Cys Leu
        275                 280                 285

Glu Glu Glu Ala Val Val Thr Tyr Thr Arg Ile Ile Ser Asp Ile Glu
    290                 295                 300

Asn Gly Tyr Val Pro Glu Trp Glu Lys Leu Pro Ala Pro Glu Ile Ala
305                 310                 315                 320

Ile Ser Tyr Trp Arg Leu Pro Pro Asp Ala Thr Phe Leu Asp Thr Leu
                325                 330                 335

Arg Ala Ile Arg Ala Asp Glu Ala Thr His Arg Phe Val Asn His Thr
            340                 345                 350

Phe Ala Ser Leu Asp Ser Lys Lys Asp Phe Asn Pro Phe Ala Ile Ala
```

-continued

```
            355                 360                 365
Glu Pro Asp Ala Thr Thr Lys Gly Ser Val Tyr Gly Phe Thr Arg Asp
        370                 375                 380

Glu Ala Ala Ala Phe Ala Gln Lys Thr Arg Glu Arg Met Ser Gln Thr
385                 390                 395                 400

Asn

<210> SEQ ID NO 2
<211> LENGTH: 3724
<212> TYPE: DNA
<213> ORGANISM: Phaffia rhodozyma
<220> FEATURE:
<221> NAME/KEY: exon
<222> LOCATION: (1407)..(1673)
<220> FEATURE:
<221> NAME/KEY: intron
<222> LOCATION: (1674)..(1769)
<220> FEATURE:
<221> NAME/KEY: exon
<222> LOCATION: (1770)..(1871)
<220> FEATURE:
<221> NAME/KEY: intron
<222> LOCATION: (1872)..(1948)
<220> FEATURE:
<221> NAME/KEY: exon
<222> LOCATION: (1949)..(2155)
<220> FEATURE:
<221> NAME/KEY: intron
<222> LOCATION: (2156)..(2264)
<220> FEATURE:
<221> NAME/KEY: exon
<222> LOCATION: (2265)..(2294)
<220> FEATURE:
<221> NAME/KEY: intron
<222> LOCATION: (2295)..(2372)
<220> FEATURE:
<221> NAME/KEY: exon
<222> LOCATION: (2373)..(2423)
<220> FEATURE:
<221> NAME/KEY: intron
<222> LOCATION: (2425)..(2515)
<220> FEATURE:
<221> NAME/KEY: exon
<222> LOCATION: (2516)..(2644)
<220> FEATURE:
<221> NAME/KEY: intron
<222> LOCATION: (2645)..(2735)
<220> FEATURE:
<221> NAME/KEY: exon
<222> LOCATION: (2736)..(2831)
<220> FEATURE:
<221> NAME/KEY: intron
<222> LOCATION: (2832)..(2914)
<220> FEATURE:
<221> NAME/KEY: exon
<222> LOCATION: (2915)..(2998)
<220> FEATURE:
<221> NAME/KEY: intron
<222> LOCATION: (2999)..(3085)
<220> FEATURE:
<221> NAME/KEY: exon
<222> LOCATION: (3086)..(3205)
<220> FEATURE:
<221> NAME/KEY: intron
<222> LOCATION: (3206)..(3320)
<220> FEATURE:
<221> NAME/KEY: exon
<222> LOCATION: (3321)..(3332)
<220> FEATURE:
<221> NAME/KEY: 5'UTR
<222> LOCATION: (1295)..(1296)
<220> FEATURE:
<221> NAME/KEY: polyA_site
<222> LOCATION: (3682)..(3683)
```

-continued

```
<400> SEQUENCE: 2
gaattcaaca ggtcaaatga gaaaggacaa ggtgaagaga tggaaccaga agcaatcagc      60
gagagtaaag acgatggttc taaacataca ttgggcacga ctcccttgat ccgaggcagg     120
tatacgacca gatacaaaaa caagctgacg gtcacggccg aaaataggaa ggagagttgc     180
aacgctcggc taaagaaggt ggattcaatc acaacacacg gtcaaggcaa gcatgacata     240
ttgagctttt gcttgagtat ctcgcgatca aagtgatgat ggatgcttct aaggatcgtc     300
tttatctttc cgccaggaga tgtgcaataa caagagagga agagaaacgt aaggagtgt      360 actcacatgc ccaaaccacc ggcgttggat tcgagaagag ctcttcttag gctgtctccg     420
acgccccaat ggcggacgcc caatagtcca aacacgatgt acttgccatt ccgaagaagg     480
ttaggaaggt atgggctcga agctgctgat tgaccagaca taggacaaga acaaataaag     540
agacaagaaa cgacaacgac cgagcagata tctgactaga gaaaaccgtg gcgacgttgc     600
aatgtttggg cccgaaaaaa gatgagttgc tttgttttcg agtcgtcctg tagccccagc     660
tggggactag ccgctgtcac gaggaaacag gcgtgggtgg atgctccacc acatggatgg     720
ttacacacgc cacactgccg cacgctgcgc agatataacc cgttcaacac ccgacaacga     780
actggttgac cttccgaggt gaccatcaag cttggatgtt cagctgcgat attcagctac     840
gatgatatgt atgccgaaca caagtagtaa aatggctcag aaagacacag aagaaacggc     900
gttcattact ccgaaagacg agacatcccc gcatgaatct ctggacgata aagccaagcg     960
gacggacgga agcccattgg cgatggtcgg ttactaaccc tgctggcttc actgcttggc    1020
ctgacttgac tgtctcttcc tcacttgctg tcttgactcg gtcgacggat aactcgccaa    1080
acccatcaac acggcagtcc gtttagattt ccgttcccac ctcttcttcg agtttccgtt    1140
catgctctac taatgcgttt actgaattca acacaatgtc taattgaatc tgctgactgt    1200
actgcctgtt gatctgaggt ttctgacact aacatgactt atcatttggc tgacttataa    1260
atagttcgag accaacagct cttaattctg atcctgccta catacatatc tactctttgc    1320
tcgaccattg catcaaacca ttgcacgctt ctctccatac tggctatatc acaataccctg   1380 ccatatacat tgcccaacta ccaaca atg tct ctt gct aga tgt ctt gtc cag    1433 gca tca act cgg tca ctt tcg cgt acc gtt cgg cca tcc tat ctc aca     1481 cct cta aca gtt cac ttc ttc tcc tca aca atc tca agg agc tgc tcc     1529 agg tca tat tca acg tcg aac acc cgc ctt tca aca tct aat ggt caa     1577 caa tca acg cat cat ctt gcg gac aat gtt cct ctc acc acc gac aaa     1625 caa agg cac ctt caa ggc gtc atc ggc ggt gag ggc atg cat cag cat     1673 ggtccgttct tctgtcctct atcatattcg tatcaaaata tggattagtt cttattcaca    1733
attctttatc tcatcaaaca tgcttactgt ccatag atg caa cga cgg tag ctc     1787 ata cgg atc cct tag ctt ccg tca tac aag att tga ctg ttc cca cta     1835 acg gat ctt ggg tga tgc ata atc ccg tct ata ctc gagtacgtct         1881 ctgaacgctt cgcttcaatt attcctgcgc tagctacagc tcaccggtcc ttctcccttt    1941 ctgacag act gag tta gat gct gtt cag gtc gtt cat cgt ccc ccc acc     1990 aac acg tcc gac caa gtc tcc acc aag ctt gtc aag atg ctc cga tgg     2038 gga ttc gac ctt gtc agc aac tac aaa cat gtt ccc ttt ccc gca aac     2086 cac aaa gaa ctc agc gtc act caa ttg cgc caa atg ggc tgt ctt ctc     2134 tcg cct gat caa tgg atg acg gttagtatta cttactcttg tcgtcagtat         2185
```

```
tcatggcaac atattgctca tctagtcaag tgcacacgtc catttcgtct aatttgttac    2245
tttttctgaa aattcacag agg ttc atc ttt cta gaa aca aca gct gct         2294 agttcgttca tccaccaaca caaccattct tgataatacc cacttttct tcgatactga    2354 tatttatact caacctag ttc ctg gaa tgg ttg gcg gtc tct tgc gcc atc      2405 ttc agt ctc tcc gac tca gttcgtttca ttctttcttc tcgattgatc             2453
atcgttttgg catcatctgt tgataagcat agtccttacg cattcgatct tgattcgttc    2513 ag tgc gac ggg atg gtg gtt gga ttc aca cgc ttc ttg ctg aag ctg       2560 aaa acg aac gtc tcc acc ttc tga cgt tca tga gca tgg cta atc cac      2608 ctc tct ggt tcc gag ctt tga tac tgg gag ctc aag ggtcagcctt           2654 ttttatcatt attaatatta atttctctct ctagacgatc acggaccatg tgctgagagg    2714
gtcttcatat atgctttgca g ggt ttt tta taa cct gtt ctt cat aac tta      2765 ttt aat ttc ccc gcc ggt ggc tca tcg att cgt tgc ctg cct gga gga      2813 aga agc tgt cgt tac tta gtaagatcga tcgttgcaat catgctcgag              2861
tagtctttta gtttgttaat cattcgattg ggattggttt cgtatttcat cag cac       2917 aag aat tat cag tga tat cga gaa cgg cta tgt acc tga atg gga aaa      2965 gct tcc cgc tcc cga gat tgc tat atc tta ctg gtctgcttga cttcagtcgc    3018
acagtttcat ttgtcttgac atgtaaattg ttactgacaa tatgctcaca aatatcacct    3078 tcatcag gcg act tcc tcc cga tgc tac ctt ttt gga cac act gcg agc      3127 cat ccg agc aga tga ggc cac tca tcg att cgt gaa tca cac att tgc      3175 cag cct gga ctc taa gaa aga ctt caa tcc agttcgtata gaccttccaa        3225
accctaactg cgcgtcctcg actgaaactt atagattgat caaatctcaa accttcattc    3285
gcctgtcatt catctctgtt tcgaaatcac ataag ttt gcg ata gcc gagccagacg    3342 ccactactaa aggctcggta tatggttca cacgggacga ggccgccgcc ttcgctcaga    3402
agacgagaga acgcatgtct cagaccaatt gatattcatc cctaattgtc ctatactctt    3462
tctcttcttc atgtttgatt ctctgtacta ttttctggcg gtttgtatag ttttatgggt    3522
caagttcggt ttcttttttt ggttgttctt ctctttccca tattgaataa aatccgtcta    3582
tgttttcctt gatcttgatt cggatcgatt gtcactcctc actcctctct cctcattcat    3642
ctactctacc tcagtcttat atgggttatg tcgcttcctt ctcaaatgac atacgcaaac    3702
tcagtatttg agaacattgt ga                                              3724
```

<210> SEQ ID NO 3
<211> LENGTH: 26
<212> TYPE: DNA
<213> ORGANISM: aox3
<220> FEATURE:
<221> NAME/KEY: N_region
<222> LOCATION: (1)..(26)
<223> OTHER INFORMATION: N = A
<220> FEATURE:
<223> OTHER INFORMATION: N = A

<400> SEQUENCE: 3
aaygarmgna tgcayytnyt nacntt                                          26

<210> SEQ ID NO 4
<211> LENGTH: 26
<212> TYPE: DNA

-continued

```
<213> ORGANISM: aox5
<220> FEATURE:
<221> NAME/KEY: N_region
<222> LOCATION: (1)..(26)
<223> OTHER INFORMATION: N = A
<220> FEATURE:
<223> OTHER INFORMATION: N = A

<400> SEQUENCE: 4
gcytcytcyt cnarrtancc nacraa                                     26

<210> SEQ ID NO 5
<211> LENGTH: 20
<212> TYPE: DNA
<213> ORGANISM: poc1

<400> SEQUENCE: 5
agctacaaca tacgaaaggg                                            20

<210> SEQ ID NO 6
<211> LENGTH: 20
<212> TYPE: DNA
<213> ORGANISM: poc2

<400> SEQUENCE: 6
ggggaactga gagctctaaa                                            20

<210> SEQ ID NO 7
<211> LENGTH: 26
<212> TYPE: DNA
<213> ORGANISM: aox13

<400> SEQUENCE: 7
gtgtcagaaa cctcagatca acaggc                                     26

<210> SEQ ID NO 8
<211> LENGTH: 26
<212> TYPE: DNA
<213> ORGANISM: aox14

<400> SEQUENCE: 8
caacaggcag tacagtcagc agattc                                     26

<210> SEQ ID NO 9
<211> LENGTH: 20
<212> TYPE: DNA
<213> ORGANISM: aox15

<400> SEQUENCE: 9
gaattcaaca ggtcaaatga                                            20

<210> SEQ ID NO 10
<211> LENGTH: 20
<212> TYPE: DNA
<213> ORGANISM: aox16

<400> SEQUENCE: 10
atccacccac gcctgtttcc                                            20

<210> SEQ ID NO 11
<211> LENGTH: 20
<212> TYPE: DNA
<213> ORGANISM: aox17

<400> SEQUENCE: 11
```

```
ggaaacaggc gtgggtggat                                              20

<210> SEQ ID NO 12
<211> LENGTH: 20
<212> TYPE: DNA
<213> ORGANISM: aox18

<400> SEQUENCE: 12
gaattcagta aacgcattag                                              20

<210> SEQ ID NO 13
<211> LENGTH: 33
<212> TYPE: DNA
<213> ORGANISM: aox101

<400> SEQUENCE: 13
ggccattatg gcctcaattg gtctgagaca tgc                               33

<210> SEQ ID NO 14
<211> LENGTH: 33
<212> TYPE: DNA
<213> ORGANISM: aox102

<400> SEQUENCE: 14
ggccgaggcg gccatgtctc ttgctagatg tct                               33

<210> SEQ ID NO 15
<211> LENGTH: 1232
<212> TYPE: DNA
<213> ORGANISM: Phaffia rhodozyma

<400> SEQUENCE: 15
ggccattatg gcctcaattg gtctgagaca tgcgttctct cgtcttctga gcgaaggcgg   60
cggcctcgtc ccgtgtgaaa ccatataccg agcctttagt agtggcgtct ggctcggcta  120
tcgcaaatgg attgaagtct ttcttagagt ccaggctggc aaatgtgtga ttcacgaatc  180
gatgagtggc ctcatctgct cggatggctc gcagtgtgtc caaaaggta gcatcgggag  240
gaagtcgcca gtaagatata gcaatctcgg gagcgggaag cttttcccat tcaggtacat  300
agccgttctc gatatcactg ataattcttg tgtaagtaac gacagcttct tcctccaggc  360
aggcaacgaa tcgatgagcc accggcgggg aaattaaata agttatgaag aacaggttat  420
aaaaaacccc ttgagctccc agtatcaaag ctcggaacca gagaggtgga ttagccatgc  480
tcatgaacgt cagaaggtgg agacgttcgt tttcagcttc agcaagaagc gtgtgaatcc  540
aaccaccatc ccgtcgcatg agtcggagag actgaagatg gcgcaagaga ccgccaacca  600
ttccaggaat agcagctgtt gtttctagaa agatgaacct cgtcatccat tgatcaggcg  660
agagaagaca gcccatttgg cgcaattgag tgacgctgag ttctttgtgg tttgcgggaa  720
agggaacatg tttgtagttg ctgacaaggt cgaatcccca tcggagcatc ttgacaagct  780
tggtggagac ttggtcggac gtgttggtgg ggggacgatg aacgacctga acagcatcta  840
actcagttcg agtatagacg ggattatgca tcacccaaga tccgttagtg gaacagtca   900
aatcttgtat gacggaagct aagggatccg tatgagctac cgtcgttgca tcatgctgat  960
gcatgccctc accgccgatg acgccttgaa ggtgcctttg tttgtcggtg gtgagaggaa 1020
cattgtccgc aagatgatgc gttgattgtt gaccattaga tgttgaaagg cgggtgttcg 1080
acgttgaata tgacctggag cagctccttg agattgttga ggagaagaag tgaactgtta 1140
```

-continued

```
gaggtgtgag ataggatggc cgaacggtac gcgaaagtga ccgagttgat gcctggacaa    1200
gacatctagc aagagacatg gccgcctcgg cc                                   1232

<210> SEQ ID NO 16
<211> LENGTH: 28
<212> TYPE: DNA
<213> ORGANISM: ast49

<400> SEQUENCE: 16
gcggccgcac gtacagacta agatcgac                                        28

<210> SEQ ID NO 17
<211> LENGTH: 33
<212> TYPE: DNA
<213> ORGANISM: ast50

<400> SEQUENCE: 17
ggccataatg gccatggaga aagtaggtgg caa                                  33

<210> SEQ ID NO 18
<211> LENGTH: 39
<212> TYPE: DNA
<213> ORGANISM: ast36

<400> SEQUENCE: 18
cctgcaggcc gcctcggccg ttgattcttc atatgttaa                            39

<210> SEQ ID NO 19
<211> LENGTH: 26
<212> TYPE: DNA
<213> ORGANISM: ast37

<400> SEQUENCE: 19
ggtaccctgc agtcgacaaa catgaa                                          26
```